US012622453B2

(12) United States Patent
Li et al.

(10) Patent No.: US 12,622,453 B2
(45) Date of Patent: May 12, 2026

(54) METHOD FOR PREPARING WATER-SOLUBLE RUTIN POWDER AND USES THEREOF

(71) Applicant: HENAN ZHONGDA HENGYUAN BIOTECHNOLOGY STOCK CO., LTD., Luohe City (CN)

(72) Inventors: Honglong Li, Luohe City (CN); Ziheng Jin, Luohe City (CN); Yanjun Wen, Luohe City (CN); Linzheng Li, Luohe City (CN); Mingming Wang, Luohe City (CN); Yulian Guo, Luohe City (CN); Haitao Han, Luohe City (CN); Di Wang, Luohe City (CN)

(73) Assignee: HENAN ZHONGDA HENGYUAN BIOTECHNOLOGY STOCK CO., LTD., Luohe City (CN)

( * ) Notice: Subject to any disclaimer, the term of this patent is extended or adjusted under 35 U.S.C. 154(b) by 424 days.

(21) Appl. No.: 18/377,793

(22) Filed: Oct. 7, 2023

(65) Prior Publication Data

US 2024/0206519 A1     Jun. 27, 2024

(30) Foreign Application Priority Data

Dec. 21, 2022    (CN) ........................ 202211648600.X

(51) Int. Cl.
| | |
|---|---|
| A61K 31/7048 | (2006.01) |
| A23L 2/52 | (2006.01) |
| A23L 29/212 | (2016.01) |
| A23L 29/25 | (2016.01) |
| A23L 29/269 | (2016.01) |
| A23L 29/30 | (2016.01) |
| A23P 10/30 | (2016.01) |
| A61K 8/60 | (2006.01) |
| A61K 9/107 | (2006.01) |
| A61K 9/16 | (2006.01) |
| A61K 47/36 | (2006.01) |
| A61Q 19/00 | (2006.01) |

(52) U.S. Cl.
CPC ................. *A23P 10/30* (2016.08); *A23L 2/52* (2013.01); *A23L 29/212* (2016.08); *A23L 29/25* (2016.08); *A23L 29/274* (2016.08); *A23L 29/35* (2016.08); *A23L 29/37* (2016.08);

*A61K 8/602* (2013.01); *A61K 9/107* (2013.01); *A61K 9/1694* (2013.01); *A61K 31/7048* (2013.01); *A61K 47/36* (2013.01); *A61Q 19/00* (2013.01); *A61K 2800/10* (2013.01)

(58) Field of Classification Search
CPC .... A61K 31/7048; A61K 47/36; A61K 47/38; A61K 47/40
See application file for complete search history.

(56) References Cited

U.S. PATENT DOCUMENTS

2007/0077308 A1 * 4/2007 Giner ...................... A61P 25/00
424/490

OTHER PUBLICATIONS

Costa et al., "Drying by spray drying in the food industry: Microencapsulation, process parameters and main carriers used" African Journal of Food Science vol. 9(9), pp. 462-470, DOI:10.5897/AJFS2015.1279 (Year: 2015).*
Ifeduba et al., "Microencapsulation of stearidonic acid soybean oil in complex coacervates modified for enhanced stability" Food Hydrocolloids vol. 51 pp. 136-145, DOI:10.1016/j.foodhyd.2015.05.008 (Year: 2015).*
Dammak et al., "Investigation into the physicochemical stability and rheological properties of rutin emulsions stabilized by chitosan and lecithin" Journal of Food Engineering vool. 229 pp. 12-20, DOI:10/1016/j.foodeng.2017.09.022 (Year: 2018).*

* cited by examiner

*Primary Examiner* — Andrea Olson

(57) ABSTRACT

A method for preparing a water-soluble rutin powder includes: heating and mixing a plant polysaccharide substance, a filler, and water to obtain a wall material solution; adding an antioxidant and a rutin powder into the wall material solution at a first temperature, followed by emulsification and dispersion, pH adjustment, and high-pressure homogenization to obtain a rutin powder emulsion; and carrying out heating fusion of the rutin powder emulsion to obtain a water-soluble rutin powder. With the preparation method, a water-soluble rutin product is obtained through emulsification, high-pressure homogenization, ultra-high-temperature fusion, drying and other processes by using modified starch and a plant polysaccharide as a wall material and rutin as a core material. The product features high rutin content, good water solubility, and high solution clarity, has good stability in an acidic solution environment, and can meet requirements of acidic transparent beverage for high clarity, high stability, and no precipitation.

8 Claims, 2 Drawing Sheets

METHOD FOR PREPARING WATER-SOLUBLE RUTIN POWDER AND USES THEREOF

This application claims priority to Chinese Patent Application No. 202211648600.X, filed on Dec. 21, 2022, which is incorporated by reference for all purposes as if fully set forth herein.

FIELD OF THE INVENTION

The invention pertains to the technical field of rutin powder microencapsulation, and relates to a method for preparing a water-soluble rutin powder and uses thereof.

DESCRIPTION OF THE RELATED ART

Rutin, also known as rutoside or vitamin P, is a natural flavonoid glycoside widely present in plants. As a natural antioxidant, rutin can scavenge free radicals, inhibit lipid peroxidation, and inhibit platelet aggregation, and has anti-inflammatory, antioxidant, anti-allergic and, antiviral effects. Clinically, rutin is often used in the prevention and treatment of cerebral hemorrhage, hypertension, retinal hemorrhage, purpura, and acute hemorrhagic nephritis. Tri-hydroxyethylrutin (troxerutin), a derivative of rutin, is clinically used in the treatment of burns, arthritis, various vascular diseases including cerebrovascular diseases, retinal edema, hemorrhage, etc. Because of its good biological activity and high safety, rutin has been used as a raw material in healthy foods or functional foods. *Sophora japonica*, a main source of rutin, has also been used as a raw material in medicines and foods.

Although rutin has good biological activity, its solubility in water is very low, and the rutin solution is prone to crystallization and precipitation in an acidic environment, leading to low absorption and bioavailability, greatly limiting the application of rutin. How to safely and effectively improve the water solubility of rutin and further improve the bioavailability of rutin has become the main direction of research on rutin. According to the published related literatures, the main research schemes on the application of rutin include liposome, micelle self-emulsification, copolymer complexation, microencapsulation in strong alkali environment, etc. For example, EP3082728 discloses a method for solubilizing rutin with polyhydroxyalkyl alcohols, CN201810525567.9 discloses a rutin-coated polymer micelle and preparation method thereof, EP3453766 discloses a method for producing flavonoid inclusion compounds, CN113304113 discloses a co-amorphous solid dispersion for improving dissolution of quercetin and preparation method thereof, and CN114271492 discloses a raw material composition of high-content rutin powder, rutin powder, and preparation method and application thereof.

Although the improved methods can improve the dissolution of rutin to a certain extent, most of the preparation processes are complex and require a large amount of chemically synthesized surfactant or the use of a strong alkaline solution, leading to the problems of high costs, complex process, low safety, poor product stability, low solution transparency, small pH tolerance range, and so on.

Therefore, how to find a more suitable modification method that can solve the problems in the existing technologies while safely and effectively improving the water solubility of rutin has become one of the urgent problems to be solved by front-line researchers and R&D enterprises.

SUMMARY OF THE INVENTION

Accordingly, the technical problem to be solved by the invention is to provide a method for preparing a water-soluble rutin powder and use of the water-soluble rutin powder. The method provided by the invention is a preparation method for obtaining a water-soluble rutin powder product with high rutin content without using any surfactant or any strong alkaline solution. The product of the invention features high rutin content, good water solubility, high solution clarity, and good stability in low pH solution environment, and particularly can meet the requirements of acidic transparent beverage for high clarity, high stability, and no precipitation.

The invention provides a method for preparing a water-soluble rutin powder, which includes:

step 1: heating and mixing a plant polysaccharide substance, a filler, and water to obtain a wall material solution;

step 2: adding an antioxidant and a rutin powder into the wall material solution at a first temperature, followed by emulsification and dispersion, pH adjustment, and high-pressure homogenization to obtain a rutin powder emulsion; and step 3: carrying out heating fusion of the rutin powder emulsion to obtain a water-soluble rutin powder.

Preferably, the plant polysaccharide substance includes one or more of pullulan, fucoidan, modified starch, a plant-based gum, and dextrin;

the modified starch includes one or more of sodium octenylsuccinate starch, hydroxypropyl starch, acetate starch, carboxymethyl starch, phosphate starch, and microporous starch;

the plant-based gum includes one or more of acacia gum, ghatti gum, and xanthan gum; and the dextrin includes resistant dextrin.

Preferably, the filler includes one or more of maltodextrin, microcrystalline cellulose, glucose syrup, white sugar, lactitol, erythritol, maltitol, sorbitol, α-cyclodextrin, β-cyclodextrin, γ-cyclodextrin, trehalose, xylooligosaccharide, maltooligosaccharide, lactose, and stachyose;

the wall material solution is a colloidal solution;

the mass concentration of the plant polysaccharide substance in the wall material solution is 5 wt % to 75 wt %; and the mass concentration of the filler in the wall material solution is 5 wt % to 75 wt %.

Preferably, the heating and mixing are carried out at a temperature of 75° C. to 100° C.;

the first temperature is 75° C. to 100° C.;

the antioxidant includes one or more of ascorbic acid, sodium erythorbate, epigallocatechin gallate (EGCG), and vitamin E; and the content in percentages by weight of the antioxidant in the water-soluble rutin powder is 0.01% to 1%.

Preferably, the emulsification and dispersion are carried out at a temperature of 75° C. to 100° C.;

the emulsification and dispersion are carried out at a rotational speed of 500 rpm to 20000 rpm;

the emulsification and dispersion are carried out for 0.5 min to 60 min; and an adjusting agent for the pH adjustment includes one or more of sodium carbonate, sodium bicarbonate, potassium carbonate, sodium hexametaphosphate, sodium tripolyphosphate, sodium polyphosphate, sodium pyro-
phosphate, and sodium citrate.

Preferably, the pH is 6.0 to 10.0;

the high-pressure homogenization is carried out at a
pressure of 0.1 MPa to 80 MPa; and the high-pressure homogenization is carried out for 1 to 5
times.

Preferably, the heating fusion is ultra-high-temperature
fusion;

the heating fusion is carried out at a temperature of 100°
C. to 135° C.;

the heating fusion is carried out at a pressure of 0 MPa to
0.5 MPa; and the heating fusion is carried out for 1 min to 60 min.

Preferably, the method further includes a drying step after
the heating fusion;

the drying includes one or more of centrifugal spray
drying, pressure spray drying, freeze drying, and hot air
drying;

the air inlet temperature in the centrifugal spray drying is
160° C. to 200° C.; and the air outlet temperature in the centrifugal spray drying
is 70° C. to 100° C.

Preferably, the water-soluble rutin powder is of a structure
having a wall material enveloping rutin powder particles;
and the wall material includes one or more of pullulan poly-
saccharide, fucoidan, modified starch, a plant-based
gum, and dextrin.

The invention also provides use of a water-soluble rutin
powder prepared by the method according to any one of the
technical schemes in foods, health foods, medicines, or
cosmetics.

The invention provides a method for preparing a water-
soluble rutin powder, including the following steps: first,
heating and mixing a plant polysaccharide substance, a filler,
and water to obtain a wall material solution; then, adding an
antioxidant and a rutin powder into the wall material solu-
tion at a first temperature, followed by emulsification and
dispersion, pH adjustment, and high-pressure homogeniza-
tion to obtain a rutin powder emulsion; and finally, carrying
out heating fusion of the rutin powder emulsion to obtain a
water-soluble rutin powder. Compared with the existing
technologies, with the method for preparing a water-soluble
rutin powder according to the invention, a water-soluble
rutin product is obtained through emulsification, high-pres-
sure homogenization, ultra-high-temperature fusion, drying
and other processes by using modified starch and a plant
polysaccharide as a wall material and rutin as a core mate-
rial. The product features high rutin content, good water
solubility, and high solution clarity, has good stability in an
acidic solution environment, and can meet the requirements
of acidic transparent beverage for high clarity, high stability,
and no precipitation. The product is suitable for use in food,
health food, medicine, cosmetics, and other fields.

With the method provided by the invention, a water-
soluble rutin powder product with high rutin content can be
obtained without using any surfactant or any strong alkaline
solution. The obtained product features high rutin content,
good water solubility, high solution clarity, and good sta-
bility in low pH solution environment, and particularly can
meet the requirements of acidic transparent beverage for
high clarity, high stability, and no precipitation. Moreover,
the preparation method has the advantages of simple pro-
cess, mild conditions, and strong controllability, and there-
fore is more suitable for industrial production.

The experimental results show that the water solubility of
the rutin powder product obtained by the invention is
significantly improved, the solution is clear and transparent,
and the rutin powder product causes no turbidity and no
precipitation in an acidic solution and has high stability and
significantly improved pH tolerance.

DETAILED DESCRIPTION OF THE PREFERRED EMBODIMENTS

Figure 1:
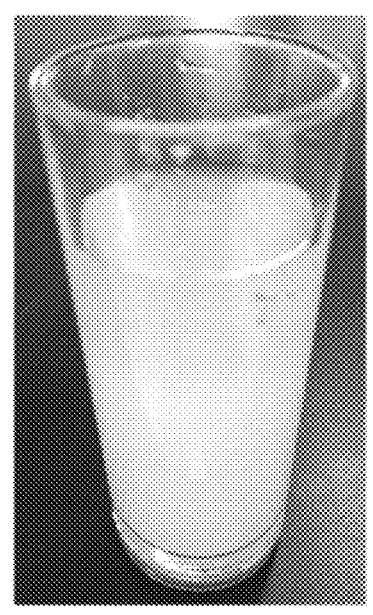
FIG. 1 illustrates images showing the dissolution effects
of ordinary rutin powder raw materials.
Figure 1:
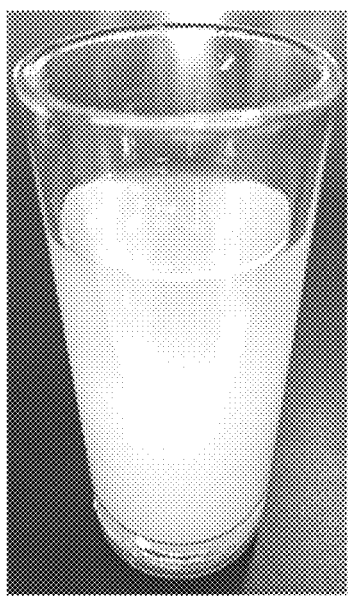
Figure 1:
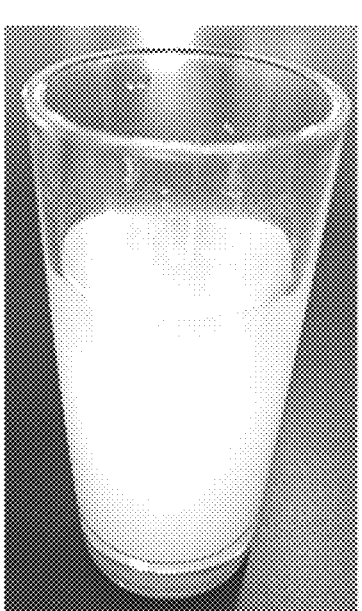

For a further understanding of the invention, preferred
examples of the invention will be described below through
examples. It should be understood that these descriptions are
merely used for further illustrating the features and advan-
tages of the invention and are not intended to limit the scope
of the invention.

Sources of all raw materials used in the invention are not
particularly limited. The raw materials may be commercially
available or prepared according to conventional methods
well known to those skilled in the art.

The purity of all the raw materials used in the invention
is not particularly limited. In the invention, the purity is
preferably technical grade or a conventional purity in the
technical field of water-solubilization of rutin powder.

All terms and abbreviations used in the invention are
conventional terms and abbreviations in the field, each of the
terms and abbreviations is clear and definite in the relevant
application field, and those skilled in the art can clearly and
accurately understand the unique meanings of the terms and
abbreviations.

The invention provides a method for preparing a water-
soluble rutin powder, which includes:

step 1: heating and mixing a plant polysaccharide sub-
stance, a filler, and water to obtain a wall material
solution;

step 2: adding an antioxidant and a rutin powder into the
wall material solution at a first temperature, followed
by emulsification and dispersion, pH adjustment, and
high-pressure homogenization to obtain a rutin powder
emulsion; and step 3: carrying out heating fusion of the rutin powder
emulsion to obtain a water-soluble rutin powder.

In the invention, first, a plant polysaccharide substance, a
filler, and water are heated and mixed to obtain a wall
material solution.

In the invention, the plant polysaccharide substance pref-
erably includes one or more of pullulan, fucoidan, modified
starch, a plant-based gum, and dextrin, and more preferably,
is pullulan, fucoidan, modified starch, a plant-based gum, or
dextrin.

In the invention, the modified starch preferably includes
one or more of sodium octenylsuccinate starch, hydroxy-
propyl starch, acetate starch, carboxymethyl starch, phos-
phate starch, and microporous starch, and more preferably, is sodium octenylsuccinate starch, hydroxypropyl starch, acetate starch, carboxymethyl starch, phosphate starch, or microporous starch.

In the invention, the plant-based gum preferably includes one or more of acacia gum, ghatti gum, and xanthan gum, and more preferably, is acacia gum, ghatti gum, or xanthan gum.

In the invention, the dextrin preferably includes resistant dextrin.

In the invention, the filler preferably includes one or more of maltodextrin, microcrystalline cellulose, glucose syrup, white sugar, lactitol, erythritol, maltitol, sorbitol, α-cyclodextrin, β-cyclodextrin, γ-cyclodextrin, trehalose, xylooligo-saccharide, maltooligosaccharide, lactose, and stachyose, and more preferably, is maltodextrin, microcrystalline cellulose, glucose syrup, white sugar, lactitol, erythritol, maltitol, sorbitol, α-cyclodextrin, O-cyclodextrin, γ-cyclodextrin, trehalose, xylooligosaccharide, maltooligosaccharide, lactose, or stachyose.

In the invention, the wall material solution is preferably a colloidal solution.

In the invention, the mass concentration of the plant polysaccharide substance in the wall material solution is preferably 5 wt % to 75 wt %, more preferably 20 wt % to 60 wt %, and more preferably 35 wt % to 45 wt %.

In the invention, the mass concentration of the filler in the wall material solution is preferably 5 wt % to 75 wt %, more preferably 20 wt % to 60 wt %, and more preferably 35 wt % to 45 wt %.

In the invention, the heating and mixing are carried out at a temperature of preferably 75° C. to 100° C., more preferably 80° C. to 95° C., and more preferably 85° C. to 90° C.

In the invention, then, an antioxidant and a rutin powder are added into the wall material solution at a first temperature, followed by emulsification and dispersion, pH adjustment, and high-pressure homogenization to obtain a rutin powder emulsion.

In the invention, the first temperature is preferably 75° C. to 100° C., more preferably 80° C. to 95° C., and more preferably 85° C. to 90° C.

In the invention, the antioxidant preferably includes one or more of ascorbic acid, sodium erythorbate, epigallocatechin gallate (EGCG), and vitamin E, and more preferably, is ascorbic acid, sodium erythorbate, EGCG, or vitamin E.

In the invention, the content in percentages by weight of the antioxidant in the water-soluble rutin powder is preferably 0.01% to 1%, more preferably 0.1% to 0.8%, and more preferably 0.3% to 0.6%.

In the invention, the emulsification and dispersion are carried out at a temperature of preferably 75° C. to 100° C., more preferably 80° C. to 95° C., and more preferably 85° C. to 90° C.

In the invention, the emulsification and dispersion are carried out at a rotational speed of preferably 500 rpm to 20000 rpm, more preferably 1000 rpm to 15000 rpm, more preferably 3000 rpm to 10000 rpm, and more preferably 4000 rpm to 7000 rpm.

In the invention, the emulsification and dispersion are carried out for preferably 0.5 min to 60 min, more preferably 5 min to 50 min, and more preferably 10 min to 30 min.

In the invention, an adjusting agent for the pH adjustment preferably includes one or more of sodium carbonate, sodium bicarbonate, potassium carbonate, sodium hexametaphosphate, sodium tripolyphosphate, sodium polyphosphate, sodium pyrophosphate, and sodium citrate, and more preferably, is sodium carbonate, sodium bicarbonate, potassium carbonate, sodium hexametaphosphate, sodium tripolyphosphate, sodium polyphosphate, sodium pyrophosphate, or sodium citrate.

In the invention, the pH is preferably 6.0 to 10.0, more preferably 6.5 to 9.5, more preferably 7.5 to 9, and more preferably 8 to 8.5.

In the invention, the high-pressure homogenization is carried out at a pressure of preferably 0.1 MPa to 80 MPa, more preferably 1 MPa to 70 MPa, more preferably 10 MPa to 60 MPa, and more preferably 20 MPa to 50 MPa.

In the invention, the high-pressure homogenization is carried out for preferably 1 to 5 times, more preferably 1 to 4 times, and more preferably 1 to 3 times.

In the invention, finally, heating fusion of the rutin powder emulsion is carried out to obtain a water-soluble rutin powder.

In the invention, the heating fusion is preferably ultrahigh-temperature fusion.

In the invention, the heating fusion is carried out at a temperature of preferably 100° C. to 135° C., more preferably 100° C. to 130° C., and more preferably 100° C. to 120° C.

In the invention, the heating fusion is carried out at a pressure of preferably 0 MPa to 0.5 MPa, more preferably 0.1 MPa to 0.3 MPa, and more preferably 0.1 MPa to 0.2 MPa.

In the invention, the heating fusion is carried out for preferably 1 min to 60 min, more preferably 5 min to 50 min, and more preferably 10 min to 40 min.

In the invention, preferably, the method further includes a drying step after the heating fusion;

In the invention, the drying preferably includes one or more of centrifugal spray drying, pressure spray drying, freeze drying, and hot air drying, and more preferably, is centrifugal spray drying, pressure spray drying, freeze drying, or hot air drying.

In the invention, the air inlet temperature in the centrifugal spray drying is preferably 160° C. to 200° C., more preferably 165° C. to 195° C., more preferably 170° C. to 190° C., and more preferably 175° C. to 185° C.

In the invention, the air outlet temperature in the centrifugal spray drying is preferably 70° C. to 100° C., more preferably 75° C. to 95° C., and more preferably 80° C. to 90° C.

In the invention, the water-soluble rutin powder is preferably of a structure having a wall material enveloping rutin powder particles. To be specific, the water-soluble rutin powder is of a structure where the wall material wraps or envelops the rutin powder particles, or is of a microencapsulation structure.

In the invention, the wall material preferably includes one or more of pullulan, fucoidan, modified starch, a plant-based gum, and dextrin, and more preferably, is pullulan, fucoidan, modified starch, a plant-based gum, or dextrin.

In the invention, to obtain a complete and detailed technical scheme, better ensure the composition and structure of the water-soluble rutin powder, and improve the water solubility of the water-soluble rutin powder and the stability of the water-soluble rutin powder in a low pH solution environment, the method for preparing a water-soluble rutin powder is preferably implemented as follows:

A method for preparing a water-soluble rutin powder, including:

step a: mixing plant polysaccharide substances such as
      modified starch, acacia gum, and dextrin with a filler and water to prepare a solution, and heating the solution to a suitable temperature to prepare a wall material solution;

step b: dissolving an antioxidant in the wall material solution at the suitable temperature with stirring, then emulsifying and dispersing a rutin powder in the resultant solution to obtain an emulsion, adding a pH adjusting agent to adjust the pH of the emulsion, and carrying out high-pressure homogenization on the rutin powder emulsion and step c: carrying out heating fusion of the homogenized rutin powder emulsion under an ultra-high temperature condition to cause the wall material to further envelop rutin, and drying to obtain a rutin powder product with good water solubility.

Specifically, in the step a, the composition of the wall material includes one or a combination of more than one of acacia gum, ghatti gum, xanthan gum, pullulan, sodium octenylsuccinate starch, hydroxypropyl starch, acetate starch, carboxymethyl starch, phosphate starch, resistant dextrin, microporous starch, and fucoidan.

Specifically, the filler is one or a combination of more than one of maltodextrin, microcrystalline cellulose, glucose syrup, white sugar, lactitol, erythritol, maltitol, sorbitol, α-cyclodextrin, β-cyclodextrin, γ-cyclodextrin, trehalose, xylooligosaccharide, maltooligosaccharide, lactose, and stachyose.

Specifically, the mass concentration of the colloidal wall material in the colloidal wall material solution is 5 wt % to 75 wt %, and the mass concentration of the filler in the colloidal wall material solution is 5 wt % to 75 wt %.

Specifically, the temperature of the wall material solution in the step a and the emulsification temperature in the step b are 75° C. to 100° C., preferably 80° C. to 95° C.

Specifically, in the step b, the antioxidant is one or more of natural antioxidants including ascorbic acid, sodium erythorbate, EGCG, and vitamin E, and is added in an amount of 0.01% to 1% of the final product.

Specifically, in the step b, the pH adjusting agent is one or a combination of more than one of sodium carbonate, sodium bicarbonate, potassium carbonate, sodium hexametaphosphate, sodium tripolyphosphate, sodium polyphosphate, sodium pyrophosphate, and sodium citrate.

Specifically, in the step b, the pH is adjusted in a range of 6.0 to 10.0, preferably 7.5 to 9.0.

Specifically, in the step b, the emulsification and dispersion are carried out at a rotational speed of 500 rpm to 20000 rpm, preferably 3000 rpm to 10000 rpm. The emulsification and dispersion are carried out for 0.5 min to 60 min, preferably 10 min to 30 min.

Specifically, in the step b, the high-pressure homogenization is carried out at a pressure of 0.1 MPa to 80 MPa, preferably 20 MPa to 50 MPa, and the high-pressure homogenization is carried out for 1 to 5 times, preferably 1 to 3 times.

Specifically, in the step c, the ultra-high-temperature fusion is carried out at a temperature of 100° C. to 135° C., preferably 100° C. to 120° C.; the ultra-high-temperature fusion is carried out at a pressure of 0 MPa to 0.5 MPa, preferably 0 MPa to 0.2 MPa; and the ultra-high-temperature fusion is carried out for 1 min to 60 min, preferably 5 min to 50 min.

Specifically, in the step c, the drying is one of centrifugal spray drying, pressure spray drying, freeze drying, and hot air drying, preferably centrifugal spray drying; the air inlet temperature in the drying is 160° C. to 200° C.; and the air outlet temperature in the drying is 70° C. to 100° C.

Further, the method for preparing a water-soluble rutin powder preferably includes:

step a: mixing plant polysaccharide substances such as modified starch, acacia gum, and dextrin with a filler and water to prepare a solution, and heating the solution to a suitable temperature to prepare a wall material solution;

step b: dissolving an antioxidant in the wall material solution at the suitable temperature with stirring, then emulsifying and dispersing a rutin powder in the resultant solution to obtain an emulsion, adding a pH adjusting agent to adjust the pH of the emulsion, and carrying out high-pressure homogenization on the rutin powder emulsion; and step c: heating the homogenized rutin powder emulsion under an ultra-high temperature condition to maintain the further fusion of rutin and the wall material, and drying to obtain a rutin powder product with good water solubility.

In the invention, first, deionized water, a colloidal wall material, and a filler are mixed to obtain a colloidal wall material solution.

The colloidal wall material is one or a combination of more than one of acacia gum, ghatti gum, xanthan gum, pullulan, sodium octenylsuccinate starch, hydroxypropyl starch, acetate starch, carboxymethyl starch, phosphate starch, resistant dextrin, microporous starch, and fucoidan.

The filler is one or a combination of more than one of maltodextrin, microcrystalline cellulose, glucose syrup, white sugar, lactitol, erythritol, maltitol, sorbitol, α-cyclodextrin, β-cyclodextrin, γ-cyclodextrin, trehalose, xylooligosaccharide, maltooligosaccharide, lactose, and stachyose.

The mass concentration of the colloidal wall material in the colloidal wall material solution is 5 wt % to 75 wt %, and the mass concentration of the filler in the colloidal wall material solution is 5 wt % to 75 wt %. The colloidal wall material solution is heated to 75° C. to 100° C., preferably 80° C. to 95° C.

The temperature of the colloidal wall material solution is kept at 75° C. to 100° C., preferably 80° C. to 95° C. In an emulsified and dispersed state, the antioxidant and the rutin powder are added for emulsification and dispersion. The pH adjusting agent is added to adjust the pH of the emulsion to 6.0 to 10.0, preferably 7.5 to 9.0. Then, high-pressure homogenization is carried out on the rutin powder emulsion to obtain a stable rutin powder emulsion.

The emulsification and dispersion are carried out at a rotational speed of 500 rpm to 20000 rpm, preferably 3000 rpm to 10000 rpm. The emulsification is carried out for 0.5 min to 60 min, preferably 10 min to 30 min. The high-pressure homogenization is carried out at a pressure of 0.1 MPa to 80 MPa, preferably 20 MPa to 50 MPa, and the high-pressure homogenization is carried out for 1 to 5 times, preferably 1 to 3 times.

The antioxidant is one or more of ascorbic acid, sodium erythorbate, EGCG, and vitamin E, and is added in an amount of 0.01% to 1% of the final product.

The pH adjusting agent is one or a combination of more than one of sodium carbonate, sodium bicarbonate, potassium carbonate, sodium hexametaphosphate, sodium tripolyphosphate, sodium polyphosphate, sodium pyrophosphate, and sodium citrate.

Then, the homogenized rutin powder emulsion is heated under an ultra-high temperature condition to maintain the further fusion of rutin and the wall material, and drying to obtain a rutin powder product with good water solubility.

The ultra-high-temperature fusion is carried out at a temperature of 100° C. to 135° C., preferably 100° C. to 120° C. The ultra-high-temperature fusion is carried out at a pressure of 0 MPa to 0.5 MPa, preferably 0 MPa to 0.2 MPa. The ultra-high-temperature fusion is carried out for 1 min to 60 min, preferably 5 min to 50 min. The drying is one of centrifugal spray drying, pressure spray drying, freeze drying, and hot air drying, preferably centrifugal spray drying. The air inlet temperature in the drying is 160° C. to 200° C. The air outlet temperature in the drying is 70° C. to 100° C.

The invention also provides a water-soluble rutin powder prepared by the method according to any one of the technical schemes.

The invention also provides use of a water-soluble rutin powder prepared by the method according to any one of the technical schemes in foods, health foods, medicines, or cosmetics.

A method for a preparing water-soluble rutin powder, a water-soluble powder rutin, and use thereof have been provided in the above content of the invention. With the method for preparing a water-soluble rutin powder according to the invention, a water-soluble rutin product is obtained through emulsification, high-pressure homogenization, ultra-high-temperature fusion, drying and other processes by using modified starch and a plant polysaccharide as a wall material and rutin as a core material. The product features high rutin content, good water solubility, and high solution clarity, has good stability in an acidic solution environment, and can meet the requirements of acidic transparent beverage for high clarity, high stability, and no precipitation. The product is suitable for use in food, health food, medicine, cosmetics, and other fields.

With the method provided by the invention, a water-soluble rutin powder product with high rutin content can be obtained without using any surfactant or any strong alkaline solution. The obtained product features high rutin content, good water solubility, high solution clarity, and good stability in low pH solution environment, and particularly can meet the requirements of acidic transparent beverage for high clarity, high stability, and no precipitation. Moreover, the preparation method has the advantages of simple process, mild conditions, and strong controllability, and therefore is more suitable for industrial production.

The experimental results show that the water solubility of the rutin powder product obtained by the invention is significantly improved, the solution is clear and transparent, and the rutin powder product causes no turbidity and no precipitation in an acidic solution and has high stability and significantly improved pH tolerance.

To further explain the invention, a method for preparing a water-soluble rutin powder and use of the water-soluble rutin powder according to the invention will be described in detail below through examples. However, it should be understood that these examples are implemented on the premise of the technical schemes of the invention, and detailed implementations and specific operation procedures are provided only for further explaining the features and advantages of the invention, but are not intended to limit the claims of the invention. The scope of protection of the invention is not limited to the following examples.

Example 1

60 g of acacia gum, 6 g of ghatti gum, 15 g of α-cyclo-dextrin, and 100 g of maltodextrin were weighed and completely dissolved in 320 g of deionized water to obtain a colloidal wall material solution A having a concentration of 35.8%, which was heated to 89° C. to 91° C. in a water bath and stirred uniformly. The temperature of the colloidal wall material solution A was kept. 0.5% (M:M) of ascorbic acid was added to the colloidal wall material solution A and stirred until they were completely dissolved. In a state of high-speed shear emulsification, 25 g of a rutin powder was added and fully emulsified and dispersed (at a rotational speed of 5500 rpm for 20 min, with the emulsion temperature being 89° C. to 91° C.). Sodium carbonate and sodium hexaphosphate were added to adjust the pH of the emulsion to 8.5 to 8.7 to obtain a rutin powder emulsion B.

High-pressure homogenization was carried on the rutin powder emulsion B (at a pressure of 45 MPa for 3 times) to obtain a stable homogeneous rutin powder solution C. Ultra-high-temperature fusion of the homogeneous rutin powder solution C was carried out at a temperature of 105° C. and a pressure of 0.05 MPa for 40 min, and then cooled to room temperature to obtain a transparent rutin powder solution D. The rutin powder solution D was spray dried to obtain a water-soluble rutin powder, where the air inlet temperature in the drying was 170° C. to 195° C., and the air outlet temperature in the drying was 80° C. to 95° C.

The tests show that the rutin powder preparation has excellent water solubility and forms a clear and transparent solution, with a rutin content of 10.6%.

Example 2

70 g of sodium octenylsuccinate starch, 5 g of hydroxy-propyl starch, 20 g of γ-cyclodextrin, 20 g of erythritol, and 70 g of maltodextrin were weighed and completely dissolved in 245 g of deionized water to obtain a colloidal wall material solution A having a concentration of 40.2%, which was heated to 83° C. to 85° C. in a water bath and stirred uniformly. The temperature of the colloidal wall material solution A was kept. 0.75% (M:M) of sodium erythorbate was added to the colloidal wall material solution A and stirred until they were completely dissolved. In a state of high-speed shear emulsification, 20 g of a rutin powder was added and fully emulsified and dispersed (at a rotational speed of 6500 rpm for 15 min, with the emulsion temperature being 83° C. to 85° C.). Potassium carbonate and sodium pyrophosphate were added to adjust the pH of the emulsion to 8.1 to 8.3 to obtain a rutin powder emulsion B.

High-pressure homogenization was carried on the rutin powder emulsion B (at a pressure of 40 MPa for 2 times) to obtain a stable homogeneous rutin powder solution C. Ultra-high-temperature fusion of the homogeneous rutin powder solution C was carried out at a temperature of 110° C. and a pressure of 0.05 MPa for 25 min, and then cooled to room temperature to obtain a transparent rutin powder solution D. The rutin powder solution D was spray dried to obtain a water-soluble rutin powder, where the air inlet temperature in the drying is 170° C. to 195° C., and the air outlet temperature in the drying is 80° C. to 95° C.

The tests show that the rutin powder preparation has excellent water solubility and forms a clear and transparent solution, with a rutin content of 10.1%.

Example 3

40 g of sodium octenylsuccinate starch, 10 g of car-boxymethyl starch, 10 g of pullulan, 20 g of xylooligosac-charide, and 70 g of maltodextrin were weighed and completely dissolved in 350 g of deionized water to obtain a colloidal wall material solution A having a concentration of 30%, which was heated to 93° C. to 95° C. in a water bath and stirred uniformly. The temperature of the colloidal wall material solution A was kept. 0.75% (M:M) of EGCG was added to the colloidal wall material solution A and stirred until they were completely dissolved. In a state of high-speed shear emulsification, 26 g of a rutin powder was added and fully emulsified and dispersed (at a rotational speed of 6000 rpm for 20 min, with the emulsion temperature being 93° C. to 95° C.). Potassium carbonate and sodium pyrophosphate were added to adjust the pH of the emulsion to 8.4 to 8.6 to obtain a rutin powder emulsion B.

High-pressure homogenization was carried on the rutin powder emulsion B (at a pressure of 35 MPa for 3 times) to obtain a stable homogeneous rutin powder solution C. Ultra-high-temperature fusion of the homogeneous rutin powder solution C was carried out at a temperature of 120° C. and a pressure of 0.05 MPa for 15 min, and then cooled to room temperature to obtain a transparent rutin powder solution D. The rutin powder solution D was spray dried to obtain a water-soluble rutin powder, where the air inlet temperature in the drying is 170° C. to 195° C., and the air outlet temperature in the drying is 80° C. to 95° C.

The tests show that the rutin powder preparation has excellent water solubility and forms a clear and transparent solution, with a rutin content of 15.2%.

Comparative Example 1

60 g of acacia gum, 6 g of ghatti gum, 15 g of α-cyclo-dextrin, and 100 g of maltodextrin were weighed and completely dissolved in 320 g of deionized water to obtain a colloidal wall material solution A having a concentration of 35.8%, which was heated to 89° C. to 91° C. in a water bath and stirred uniformly. The temperature of the colloidal wall material solution A was kept. 0.5% (M:M) of ascorbic acid was added to the colloidal wall material solution A and stirred until they were completely dissolved. In a state of high-speed shear emulsification, 25 g of a rutin powder was added and fully emulsified and dispersed (at a rotational speed of 5500 rpm for 20 min, with the emulsion temperature being 89° C. to 91° C.). Sodium carbonate and sodium hexaphosphate were added to adjust the pH of the emulsion to 8.5 to 8.7 to obtain a rutin powder emulsion B.

High-pressure homogenization was carried on the rutin powder emulsion B (at a pressure of 45 MPa for 3 times) to obtain a stable homogeneous rutin powder solution C. The rutin powder solution C was spray dried to obtain a water-soluble rutin powder, where the air inlet temperature in the drying was 170° C. to 195° C., and the air outlet temperature in the drying was 80° C. to 95° C.

The tests show that the rutin powder preparation has excellent water solubility and forms a turbid solution, with a rutin content of 10.8%.

Comparative Example 2

70 g of sodium octenylsuccinate starch, 5 g of hydroxy-propyl starch, 20 g of γ-cyclodextrin, 20 g of erythritol, and 70 g of maltodextrin were weighed and completely dissolved in 245 g of deionized water to obtain a colloidal wall material solution A having a concentration of 40.2%, which was heated to 83° C. to 85° C. in a water bath and stirred uniformly. The temperature of the colloidal wall material solution A was kept. 0.75% (M:M) of sodium erythorbate was added to the colloidal wall material solution A and stirred until they were completely dissolved. In a state of high-speed shear emulsification, 20 g of a rutin powder was added and fully emulsified and dispersed (at a rotational speed of 6500 rpm for 15 min, with the emulsion temperature being 83° C. to 85° C.). Potassium carbonate and sodium pyrophosphate were added to adjust the pH of the emulsion to 8.1 to 8.3 to obtain a rutin powder emulsion B.

High-pressure homogenization was carried on the rutin powder emulsion B (at a pressure of 40 MPa for 2 times) to obtain a stable homogeneous rutin powder solution C. The rutin powder solution C was spray dried to obtain a water-soluble rutin powder, where the air inlet temperature in the drying was 170° C. to 195° C., and the air outlet temperature in the drying was 80° C. to 95° C.

The tests show that the rutin powder preparation has excellent water solubility and forms a turbid solution, with a rutin content of 10.3%.

Comparative Example 3

70 g of sodium octenylsuccinate starch, 5 g of hydroxy-propyl starch, 20 g of γ-cyclodextrin, 20 g of erythritol, and 70 g of maltodextrin were weighed and completely dissolved in 245 g of deionized water to obtain a colloidal wall material solution A having a concentration of 40.2%, which was heated to 83° C. to 85° C. in a water bath and stirred uniformly. The temperature of the colloidal wall material solution A was kept. 0.75% (M:M) of sodium erythorbate was added to the colloidal wall material solution A and stirred until they were completely dissolved. In a state of high-speed shear emulsification, 20 g of a rutin powder was added and fully emulsified and dispersed (at a rotational speed of 6500 rpm for 15 min, with the emulsion temperature being 83° C. to 85° C.), to obtain a rutin powder emulsion B.

High-pressure homogenization was carried on the rutin powder emulsion B (at a pressure of 40 MPa for 2 times) to obtain a stable homogeneous rutin powder solution C. The rutin powder solution C was spray dried to obtain a water-soluble rutin powder, where the air inlet temperature in the drying was 170° C. to 195° C., and the air outlet temperature in the drying was 80° C. to 95° C.

The tests show that there are a lot of insoluble substances in the aqueous solution of the rutin powder preparation, and the content of rutin is 10.2%.

FIG. 1 illustrates images showing the dissolution effects of ordinary rutin powder raw materials, corresponding to the rutin contents of 0.33%, 0.66%, 1.33% (M:M) from left to right.

Figure 2:
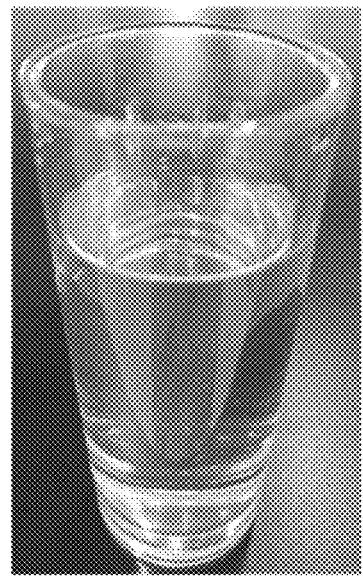
FIG. 2 illustrates images showing the dissolution effects
of water-soluble rutin powders prepared according to
examples of the invention.
Figure 2:
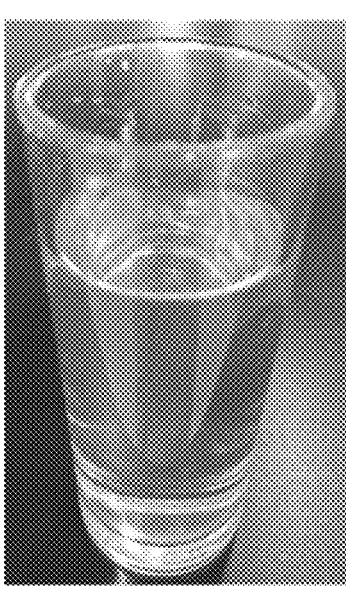
Figure 2:

FIG. 2 illustrates images showing the dissolution effects of water-soluble rutin powders prepared according to examples of the invention, corresponding to the rutin contents of 0.33%, 0.66%, 1.33% (M:M) from left to right.

Figure 3:
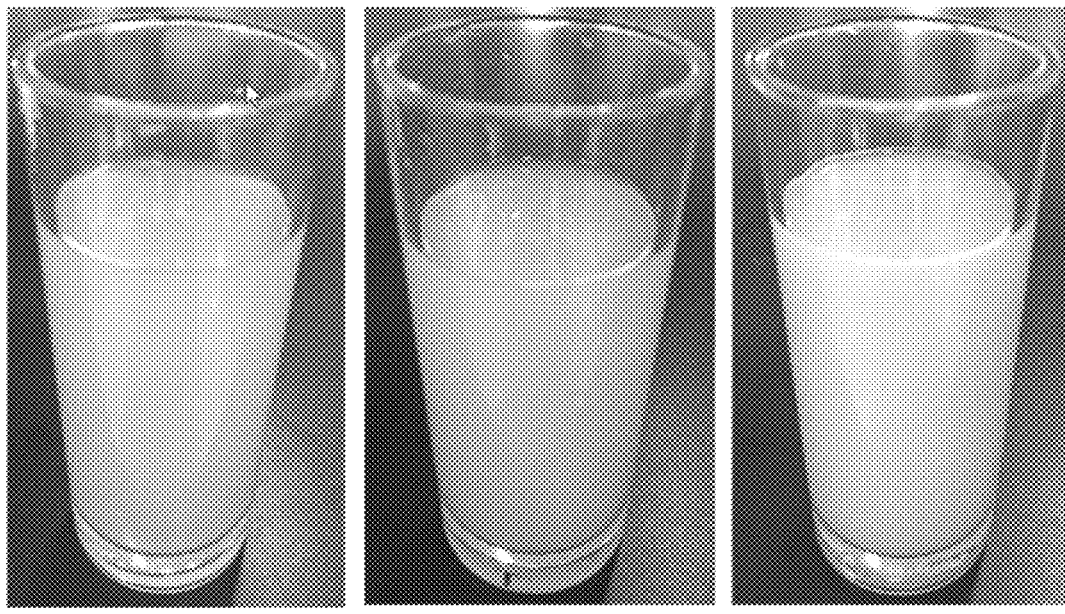
FIG. 3 illustrates images showing the dissolution effects
of rutin powders prepared according to comparative
examples of the invention.

FIG. 3 illustrates images showing the dissolution effects of rutin powders prepared according to comparative examples of the invention, corresponding to the rutin contents of 0.33%, 0.66%, 1.33% (M:M) from left to right.

The detailed statistics on the effects of the examples and comparative examples are shown in Table 1.

Refer to Table 1, which provides statistics on the differences between and the effects of the examples and comparative examples of the invention.

TABLE 1

| | Difference | Content | Solubility | Transmittance of 1% solution |
|---|---|---|---|---|
| Example 1 | Emulsion at 90° C. for 20 min, pH 8.6, homogenization at 45 MPa for 3 times, high-temperature fusion at 105° C. for 40 min | 10.6% | Water soluble, clear and transparent | 96.2% |
| Example 2 | Emulsion at 84° C. for 15 min, pH 8.2, homogenization at 40 MPa for 2 times, high-temperature fusion at 110° C. for 25 min | 10.1% | Water soluble, clear and transparent | 98.1% |
| Example 3 | Emulsion at 94° C. for 20 min, pH 8.5, homogenization at 35 MPa for 3 times, high-temperature fusion at 120° C. for 15 min | 15.2% | Water soluble, clear and transparent | 97.4% |
| Comparative Example 1 | Emulsion at 90° C. for 20 min, pH 8.6, homogenization at 45 MPa for 3 times | 10.8% | Turbid solution | 3.6% |
| Comparative Example 2 | Emulsion at 84° C. for 15 min, pH 8.2, homogenization at 40 MPa for 2 times | 10.3% | Turbid solution | 4.7% |
| Comparative Example 3 | Emulsion at 84° C. for 15 min, homogenization at 40 MPa for 2 times | 10.2% | A large amount of insoluble substances | 2.2% |

The application effect and stability of the above examples and comparative examples were tested in solid beverages and acidic beverages respectively.

Application in solid beverage and test method: A base powder (including freeze-dried apple powder, white sugar, erythritol, citric acid, sodium citrate, maltodextrin, etc.) of an apple flavor solid beverage was formulated. 5% of each of the samples obtained in the examples and comparative examples of the invention was added to the base powder and mixed uniformly. Each of the resultant mixtures were packed in sachets of 10 g, and placed in a thermostatic oven at 45° C. The stability and solubility of the mixtures after different storage periods were tested.

Application in acidic liquid beverage and test method: A base material (including apple concentrated juice, white sugar, erythritol, citric acid, sodium citrate, pectin, water, etc.) with a pH value of 3.2 to 3.4 of an acidic liquid beverage was formulated. 0.4% of each of the samples obtained in the examples and comparative examples of the invention was added to the base material. After dissolution, filtration, sterilization at 95° C. for 30 min, hot filling, cooling and other processes, the resultant mixtures were packed in PET bottles (300 mL/bottle) and allowed to stand indoors.

The stability of the mixtures after different storage periods were tested. The comparison of the application effects of the examples and comparative examples of the invention is shown in Table 2 and Table 3.

Refer to Table 2, which shows the application of the examples and comparative examples of the invention in solid beverages.

TABLE 2

| | | Initial | 3 months | 6 months |
|---|---|---|---|---|
| Dissolution effect | Examples | Readily soluble, transparent solution | Readily soluble, transparent solution | Readily soluble, transparent solution |
| | Comparative Example | Turbid solution with insoluble substances | Turbid solution with insoluble substances | Turbid solution with insoluble substances |
| Rutin content | Examples | 0.51% | 0.507% | 0.502% |
| | Comparative Example | 0.515% | 0.510% | 0.502% |

Refer to Table 3, which shows the application of the examples and comparative examples of the invention in acidic liquid beverages.

TABLE 3

| | | Initial | 3 months | 6 months |
|---|---|---|---|---|
| Solution state | Examples | Transparent, clear | Transparent, clear, no precipitation | Transparent, clear, no precipitation |
| | Comparative Example | Turbid, with a small amount of insoluble substances | Turbid, with a large amount of precipitate | Turbid, with a large amount of precipitate |

TABLE 3-continued

|  |  | Initial | 3 months | 6 months |
|---|---|---|---|---|
| Rutin content | Examples | 0.044‰ | 0.044‰ | 0.041‰ |
|  | Comparative Example | 0.037‰ | 0.028‰ | 0.019‰ |

As can be seen from the effects of application in solid beverages and transparent acidic liquid beverages in Table 2 and Table 3, the examples of the invention can meet the requirements of application and stability, and the products are stable during the shelf life.

A method for preparing a water-soluble rutin powder and use of the water-soluble rutin powder according to the invention have been described above in detail. Although the principles and implementations of the invention are described by using specific examples in this specification, the descriptions of the foregoing examples are only for the purpose of helping understand the method of the invention and its core idea, including the best mode, and enabling those skilled in the art to practice the invention, including the manufacture and use of any device or system and the implementation of any combined method. It should be noted that some improvements and modifications can be made by those skilled in the art without departing from the principles of the invention, and such improvements and modifications also fall within the scope of protection of the claims of the invention. The scope of protection of the invention is defined by the claims and may include other examples that are conceivable to those skilled in the art. These other examples shall also fall within the scope of the claims, provided that they have structural elements that are not different from the literal representation of the claims or they include equivalent structural elements that substantially are not different from the literal representation of the claims.

What is claimed is:

1. A method for preparing a water-soluble rutin powder, comprising:
   step 1: heating and mixing a plant polysaccharide substance, a filler, and water to obtain a wall material solution;
   step 2: adding an antioxidant and a rutin powder into the wall material solution at a first temperature, followed by emulsification and dispersion, pH adjustment, and high-pressure homogenization to obtain a rutin powder emulsion; and
   step 3: carrying out heating fusion of the rutin powder emulsion to obtain the water-soluble rutin powder,
   wherein the heating and mixing are carried out at a temperature of 75° C. to 100° C.;
   the first temperature is 75° C. to 100° C.;
   the antioxidant is one or more selected from the group consisting of ascorbic acid, sodium erythorbate, epigallocatechin gallate (EGCG), and vitamin E; and
   a content in percentages by weight of the antioxidant in the water-soluble rutin powder is 0.01% to 1%.

2. The method according to claim 1, wherein the plant polysaccharide substance is one or more selected from the group consigning of pullulan, fucoidan, modified starch, a plant-based gum, and dextrin;
   the modified starch is one or more selected from the group consisting of sodium octenylsuccinate starch, hydroxypropyl starch, acetate starch, carboxymethyl starch, phosphate starch, and microporous starch;

the plant-based gum comprises one or more of acacia gum, ghatti gum, and xanthan gum; and
   the dextrin comprises resistant dextrin.

3. The method according to claim 1, wherein the filler is one or more selected from the group of maltodextrin, microcrystalline cellulose, glucose syrup, white sugar, lactitol, erythritol, maltitol, sorbitol, α-cyclodextrin, β-cyclodextrin, γ-cyclodextrin, trehalose, xylooligosaccharide, maltooligosaccharide, lactose, and stachyose;
   the wall material solution is a colloidal solution;
   a mass concentration of the plant polysaccharide substance in the wall material solution is 5 wt % to 75 wt %; and
   a mass concentration of the filler in the wall material solution is 5 wt % to 75 wt %.

4. The method according to claim 1, wherein the emulsification and dispersion are carried out at a temperature of 75° C. to 100° C.;
   the emulsification and dispersion are carried out at a rotational speed of 500 rpm to 20000 rpm;
   the emulsification and dispersion are carried out for 0.5 min to 60 min; and
   an adjusting agent for the pH adjustment comprises one or more of sodium carbonate, sodium bicarbonate, potassium carbonate, sodium hexametaphosphate, sodium tripolyphosphate, sodium polyphosphate, sodium pyrophosphate, and sodium citrate.

5. The method according to claim 1, wherein in the pH adjustment, the pH of the wall material solution is 6.0 to 10.0;
   the high-pressure homogenization is carried out at a pressure of 0.1 MPa to 80 MPa; and
   the high-pressure homogenization is carried out for 1 to 5 times.

6. The method according to claim 1, wherein the heating fusion is ultra-high-temperature fusion;
   the heating fusion is carried out at a temperature of 100° C. to 135° C.;
   the heating fusion is carried out at a pressure of 0 MPa to 0.5 MPa; and
   the heating fusion is carried out for 1 min to 60 min.

7. The method according to claim 1, wherein the method further comprises a drying step after the heating fusion;
   the drying step comprises one or more of centrifugal spray drying, pressure spray drying, freeze drying, and hot air drying;
   wherein when the drying step comprises the centrifugal spray drying;
   the air inlet temperature in the centrifugal spray drying is 160° C. to 200° C.; and
   the air outlet temperature in the centrifugal spray drying is 70° C. to 100° C.

8. The method according to claim 1, wherein the water-soluble rutin powder is of a structure having a wall material enveloping rutin powder particles; and
   the wall material is one or more selected from the group consisting of pullulan, fucoidan, modified starch, a plant-based gum, and dextrin.

* * * * *